United States Patent [19]

Kerr et al.

[11] Patent Number: 5,017,274
[45] Date of Patent: May 21, 1991

[54] METHOD AND SYSTEMS FOR EXTRACTING OXYGEN EMPLOYING ELECTROCATALYSTS

[75] Inventors: John B. Kerr, Oakland; Emory S. De Castro, Emeryville; Bruce Zenner, Hercules, all of Calif.

[73] Assignee: Aquanautics Corporation, Alameda, Calif.

[21] Appl. No.: 383,381

[22] Filed: Jul. 20, 1989

Related U.S. Application Data

[63] Continuation-in-part of Ser. No. 18,888, Feb. 25, 1987, abandoned.

[51] Int. Cl.$^5$ ............................................. C25B 1/02
[52] U.S. Cl. .................... 204/129; 204/130; 204/233; 204/242; 204/275; 204/278; 252/188.28; 219/219; 55/36; 423/579
[58] Field of Search ............. 204/129, 130, 180.1, 204/182.3, 182.5, 233, 23, 252, 263, 266, 149, 242, 275, 278; 252/188.28; 261/101, DIG. 28; 422/48; 423/219, 579; 55/16, 37, 58, 59, 36; 542/2, 10, 11, 12; 548/101, 108, 109, 402; 556/13, 14, 16, 42, 44, 45, 49, 50, 51, 57, 110, 113, 136, 137, 138, 146; 544/4, 7, 66, 64

[56] References Cited

U.S. PATENT DOCUMENTS

| | | | |
|---|---|---|---|
| 3,657,082 | 4/1972 | Wells et al. | 204/130 |
| 4,451,270 | 5/1984 | Roman | 55/38 |
| 4,542,010 | 9/1985 | Roman et al. | 423/579 |
| 4,602,987 | 7/1986 | Bonaventura et al. | 204/129 |
| 4,609,383 | 9/1986 | Bonaventura et al. | 55/16 |
| 4,629,544 | 12/1986 | Bonaventura et al. | 204/131 |

OTHER PUBLICATIONS

Doblhofer and Durr, J. Electrochem. Soc. (1980) 127:1041.
Dubois, et al., J. Electroanal. Chem. (1981), 117:233.
Oyama and Anson, J. Electrochem. Soc. (1980) 127:640.
Calabrese, et al., J. Am. Chem. Soc. (1983) 105:5594–5600.
Murray, Acc. Chem. Res. (1980) 13:135.
*Comprehensive Treatise of Electrochemistry,* vol. 4, Chap. 10, p. 479.
Barton and Harrison, Carbon (1975) 13:283–288.
Panzer, Electrochimica Acta (1975) 20:635–647.
Bensenhard and Fritz, Angew. Chem. Int. Ed. Engl. (1983) 22:950–975.
Mattson and Mark, Jr., J. Coll. Inter. Sci. (1969) 31:131–144.
Weinberg and Reddy, J. App. Electrochem. (1973) 3:73–75.
Vasquez and Imai, Bioelectrochem. Bioener. (1985) 14:389–403.
Hollax and Cheng, Carbon (1985) 23:655–664.
Engstrom, Anal. Chem. (1982) 54:2310–2314.
Blaedel and Schieffer, J. Electroanal. Chem. (1977) 80:259–271.
Proctor and Sherwood, Carbon (1983) 21:53–59.
Audrieux et al., J. Am. Chem. Soc. (1979) 101:3431–3441.
Audrieux et al., J. Am. Chem. Soc. (1984) 106:1957–1962.
Saveant and Binh, J. Electroanal. Chem. (1978) 88:27–41.

*Primary Examiner*—John F. Niebling
*Assistant Examiner*—Kathryn Gorgos
*Attorney, Agent, or Firm*—Townsend and Townsend

[57] ABSTRACT

Oxygen is extracted from a fluid mixture feedstock by circulating a carrier fluid from an oxygen loading station to an electrochemical cell. The carrier fluid includes a carrier compound capable of reversibly binding oxygen, with oxygen binding dependent on the oxidation state of the compound. Oxygen bound to the carrier compound in a first oxidation state is released as the oxidation state is altered at the first electrode of the electrochemical cell. The carrier compound is then returned to the first oxidation state at the second electrode at the electrochemical cell. The loading station typically comprises an oxygen-permeable membrane which prevents bulk mixing of the fluid mixture and the carrier fluid. By providing an electrocatalyst capable of rapid electron transfer and having an electropotential less than that of the carrier compound, without binding or otherwise interfering with the carrier compound, low energy electron transfer between the carrier compounds and the electrodes of the electrochemical cell is achieved.

31 Claims, 4 Drawing Sheets

MCF

DCF

HMF

DAMF

MDAMF

METHOD AND SYSTEMS FOR EXTRACTING OXYGEN EMPLOYING ELECTROCATALYSTS

This application is a continuation-in-part of application Ser. No. 018,888, filed on Feb. 25, 1987, now abandoned.

BACKGROUND OF THE INVENTION

1. Field of the Invention

The present invention relates generally to systems and method for extracting gases from fluid mixtures. More particularly, the invention relates to the electrochemical extraction of oxygen employing electrocatalysts which promote oxygen release by facilitating electron transfer to and from carrier compounds which reversibly bind the oxygen.

Purified gases, such as oxygen, are useful in a number of industrial, scientific and medical applications. Such gases may be obtained in a variety of ways. Large-scale extraction of gases from air may be accomplished by cryogenic fractionalization where the air is liquified and separated based on the differing boiling points of its constituent gases. Although practical for producing large volumes of gases, cryogenic fractionalization is impractical for supplying small gas volumes, particularly at remote or inaccessible locations.

As an alternative to cryogenic fractionalization, a variety of small-scale techniques have been developed for producing relatively pure gases. For example, hydrogen and oxygen may be produced by the electrolysis of water under controlled conditions. Although practical for many applications, electrolysis suffers from relatively high energy requirements and a substantial danger of explosion resulting from the presence of molecular hydrogen. Methods have also been developed for extracting dissolved gases from liquids, particularly fresh sea water. Such methods generally employ gas-permeable membrane for extracting the gases. As with electrolysis, membrane gas extraction is useful, but suffers from a number of limitations. In particular, most membranes are nonselective and will pass whatever gases are dissolved in the sea water. Moreover, the pressure of the collected gas generally cannot exceed the partial pressure in the sea water, at least in the absence of suitable compression and storage equipment.

Recently, systems have been developed for extracting oxygen from fluid mixture feedstocks based on the use of transition metal coordination compounds which in a first oxidation state bind the oxygen molecules and in a second oxidation state release the oxygen molecules. The systems, as described in U.S. Pat. Nos. 4,602,987, 4,609,383, and 4,629,544 rely on circulating the carrier compounds past a first location where the oxygen is bound, typically through an oxygen-permeable membrane. The oxygen-loaded carrier compounds are circulated past a first electrode where their oxidation state is changed, causing release of the oxygen which may be then collected and stored or utilized. The unloaded carrier compounds are then circulated past the second electrode of the electrochemical cell, where they are returned to their first oxidation state. The carrier compounds are then returned to the loading station where they can again bind oxygen from the fluid mixture.

Such systems have several advantages. First, the energy requirement is low relative to other extraction techniques, particularly electrolytic decomposition of water. Second, the partial pressure of oxygen which may be obtained is limited only by the solubility of the organometallic carriers in the circulating carrier fluid. Thus, oxygen pressures which are much higher than the partial pressure in the fluid mixture may be obtained without use of supplemental compression equipment.

Despite the substantial advance represented by U.S. Pat. Nos. 4,602,987, 4,609,383, and 4,629,544, it would still be desirable to provide improvements in the systems described. In particular, it would be desirable to enhance oxygen extraction by promoting the transfer of electrons from the carrier compounds to the anodic electrode and/or from the cathodic electrode to the carrier compounds. Such promotion would increase the volume output of oxygen from a fixed sized cell or, alternatively, allow a fixed amount of oxygen to be produced by a cell having reduced electrode area and/or lower power consumption.

2. Description of the Background Art

Various electrochemically active transition metal complexes and organic substances can be bound to or incorporated in electrode surfaces. For example, Doblhofer and Durr, J. Electrochem. Soc. (1980) 127:1041, disclose codeposition of acrylonitrile monomers with metal acetylacetonates on glassy carbon electrodes to form an electrode surface for cathodic reduction of molecular oxygen. Dubois, et al., J. Electroanal. Chem. (1981) 117:233, disclose ferrocene derivatives covalently linked to polytyramine films and their electrochemical properties. Oyama and Anson, J. Electrochem. Soc. (1980) 127:640, disclose the electrochemical characteristics of ruthenium complexes bound to poly-(4-vinylpyridine) coated electrodes. Naphthaquinones have been bound to an electrode surface and used to catalyze the reduction of $O_2$ to $H_2O_2$ Calabrese, et al., J. Am. Chem. Soc. (1983) 105:5594–5600. Methods of preparing chemically modified electrodes are reviewed by Murray, Acc. Chem. Res. (1980) 13:135.

A number of surface groups have been identified on carbon electrodes, including carboxyl, phenolic hydroxyl, quinone, normal lactone, fluorescein-like lactone, carboxylic anhydride, and cyclic peroxide (*Comprehensive Treatise of Electrochemistry*, Vol. 4, Chap. 10, p. 479); cyclic esters (Barton and Harrison, Carbon (1975) 13:283–288); quinoid, quihydrone, phenolic, carboxyl, carbonyl, lactone, sulfates, metal acid derivatives, and lamellar compounds (Panzer, Electrochimica Acta (1975) 20:635–647); (carboxyl, alcoholic, phenolic hydroxyl, quinones, and lactones (Bensenhard and Fritz, Angew. Chem. Int. Ed. Engl. (1983) 22:950–975); and ketone carbonyl groups (Mattson and Mark, Jr., J. Coll. Inter. Sci. (1969) 31:131–144).

The surfaces of carbon electrodes have been modified by a number of techniques, including electrochemical oxidation (Weinberg and Reddy J. App. Electrochem. (1973) 3:73–75; Vasquez and Imai, Bioelectrochem. Bioener. (1985) 14:389–403; and U.S. Pat. No. 3,657,082); oxidation in a heated airstream (Hollax and Cheng, Carbon (1985) 23:655–664); voltage cycling with a planar electrode surface Engstrom, Anal. Chem. (1982) 54:2310–2314; Blaedel and Schieffer, J. Electroanal. Chem. (1977) 80:259–271); and acid oxidation of carbon fibers (Proctor and Sherwood, Carbon (1983) 21:53–59). Various pretreatments have been reported to increase electron transfer rates to certain couples (Engstrom, supra, and Blaedel and Schieffer, supra).

The mechanism of electrochemical catalysts in promoting the reduction of carbon-halogen bonds is described in Andrieux et al , J. Am. Chem. Soc. (1979) 101:3431–3441, and (1984) 106:1957–1962, and Saveant and Binh, J. Electroanal. Chem. (1978) 88:27–41.

SUMMARY OF THE INVENTION

Oxygen is extracted from a fluid mixture feedstock using a circulating carrier fluid which includes a carrier compound capable of reversibly binding oxygen. The carrier compound is typically a transition metal coordination compound which can exist in a first oxidation state (usually reduced) in which molecular oxygen is bound and in a second oxidation state (usually oxidized) in which molecular oxygen is released. By exposing the carrier fluid to the feedstock while the carrier compound is in its first oxidation state, the molecular oxygen in the fluid mixture will be extracted. By thereafter exposing the carrier fluid to a first electrode of an electrochemical cell, the oxidation state of the carrier compound is reversed and the bound oxygen is released. By then exposing the carrier fluid to the second electrode of the cell, the carrier compound is returned to its first oxidation state so that it can be recirculated to again bind oxygen from the feedstock.

The present invention relies on the use of an electrocatalyst to promote electron transfer between the carrier compounds and either or both of the electrodes of the electrochemical cell. The electrocatalyst is a substance capable of rapid electron transfer which has an electrical potential less than that of the carrier compounds under the operating conditions of the cell. That is, the energy required to transfer electrons to and from the electrocatalyst will be less than that required to transfer electrons to and from the carrier compounds directly. The electrocatalyst may be immobilized on either or both of the electrodes or, more usually, will be present in the carrier fluid so that it circulates together with the carrier compounds. Alternatively, the electrocatalysts may be bound to a support substrate outside of the electrochemical cell, and flow of the carrier fluid can be isolated from the electrochemical cell by using unbound electrocatalyst (or other mediator) to charge the immobilized electrocatalysts, and separately exposing the immobilized electrocatalyst to release the bound oxygen.

As just described, the voltage required to operate the electrochemical cell is decreased as a result of substituting the oxidation/reduction of an electrochemical catalyst having a lesser potential than that of the carrier compound. In order to retain a reasonable equilibrium in favor of formation of the second oxidation state of the carrier compound, however, it is necessary that the standard potential not be reduced too greatly. For most of the electrocatalysts described below, the difference between the standard potential of the electrocatalysts and that of the oxygenated carrier complex should be in the range from about $-0.5$ to $-0.2$ volts, more usually from about $-0.4$ to $-0.3$ volts.

DESCRIPTION OF THE SPECIFIC EMBODIMENTS

According to the present invention, molecular oxygen is obtained by electrochemical oxidation/reduction of a transition metal carrier compound used to extract oxygen from the environment. In a first oxidation state, the carrier compound binds oxygen while in a second oxidation state, the carrier compound releases oxygen. The invention lies in the use of certain electrochemical catalysts to promote the transfer of electrons between the electrodes of an electrochemical cell and the carrier compounds. Such promotion, in turn, reduces the energy required to drive the necessary redox reactions.

Apparatuses of the type generally employed in the present invention are described in U.S. Pat. Nos. 4,609,383 and 4,629,544, the disclosures of which are incorporated herein by reference. The apparatuses include an electrochemical cell having a pair of electrodes in a container defining a flow path from a first electrode to a second electrode. The electrodes are connected to a voltage or a current source in order to define an anode for oxidizing the transition metal carrier and a cathode for reducing the carrier. The flow path is in series with a loading station, and a carrier fluid is continuously circulated between the electrochemical cell and the loading station. The carrier fluid includes the transition metal carrier compound which is capable of reversibly binding oxygen and transporting the bound oxygen from the loading station to the electrochemical cell. At the first electrode of the electrochemical cell, the carrier compound is changed from a first oxidation state (in which the compound binds oxygen) to a second oxidation state (in which the compound does not bind oxygen). As a result of the changed oxidation state, bound oxygen is released from the carrier compound and collected, as described in more detail in the cited patents. The carrier fluid then passes to the second electrode, where the oxidation state of the carrier compound is reversed so that it is again capable of binding oxygen. For most of the carrier compounds described hereinafter, oxygen binding occurs in the lower valence (reduced) state, while oxygen release occurs in the higher valence (oxidized) state. Thus, the first electrode of the electrochemical cell will usually act as an anode and the second electrode will usually act as a cathode.

The loading station must be able to expose the carrier fluid to a fluid mixture feedstock including the oxygen without allowing mixing of the two fluids. Conveniently, oxygen-permeable membranes are employed which allow oxygen to diffuse from the fluid mixture feedstock to the carrier fluid without allowing mixing. The use of oxygen-permeable membranes is particularly effective with liquid feedstocks containing dissolved oxygen, such as sea water. Silicone rubber is suitable as the membrane in such applications. In the case of gaseous mixtures, such as air, it will sometimes be possible to expose the gas mixture directly to the carrier fluid, e.g., by bubbling. The carrier compound can then be relied on to selectively extract the oxygen in preference to the other gaseous species. If suitably selective carrier compounds are not available, it will be necessary to employ selective barriers.

The apparatus of the present invention is generally completed with a collector near the first electrode which is intended to receive the gas released from the carrier fluid. Also, a pump will normally be provided for circulating the carrier fluid between the electrochemical cell and loading station. Suitable pumps and collectors are described in the aforementioned U.S. Patents.

Figure 1:
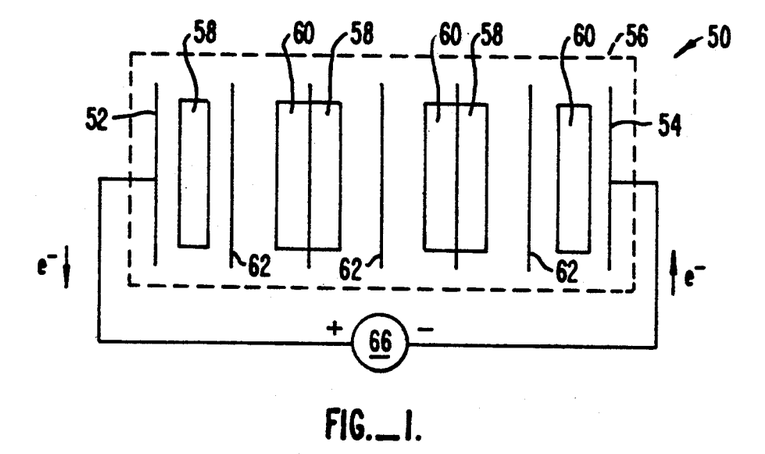
FIG. 1 is a schematic illustration of a bipolar cell useful for extracting oxygen from an oxygenated carrier compound according to the present invention.

Referring to FIG. 1, it is frequently desirable to employ a bipolar stack 50 of electrodes as the electrochemical cell of the present invention. The bipolar stack 50 includes a pair of conductor plates 52 and 54 located within a cell enclosure 56. A plurality of anodes 58 and cathodes 60 are positioned alternately between the conductive plates 50. Adjacent anode/cathode pairs 58/60 are separated by ion-permeable membranes 62, and individual anodes and cathodes may be separated by membranes 64, or may be a unitary structure having one side which functions as an anode and the other side which functions as a cathode. A voltage (or current) source 66 is connected across the conductor plates 50, and a voltage drop is induced across adjacent anode/cathode pairs 58/60. Usually, the voltage drops will be substantially equal and chosen to provide sufficient current density to evolve the desired volume of oxygen at each anode 58. With the bipolar stack 50, the total operating voltage will be greater than that for cells including a single set of one anode and one cathode. The increase will be proportional to the number of anode/cathode pairs. The current flow, however, will remain essentially the same and the overall power consumption per unit of oxygen will be the same or reduced. The advantage to using a bipolar stack is primarily that increased electrode surface areas can be obtained in a single operating unit.

In the present invention, the substance used as the electrocatalyst may be any atomic species, compound, or aggregate which fulfills certain physical requirements. The substance must be able to rapidly transfer electrons between the electrodes and the carrier compound in order to allow indirect oxidation/reduction of the carrier compound. Additionally, the electrical potential required to transfer electrons between the electrodes and the electrocatalyst must be less than that required for electron transfer between the electrodes and the carrier compounds under the operating conditions of the cell. Usually, this corresponds to a lower standard potential for the electrocatalyst than for the oxygenated carrier compound. For dual-binding carrier compounds (CC), as described in more detail hereinbelow, the standard half-cell reaction would be written as follows for the initial oxidation of the oxygenated complex:

$$CC(II)-O_2-CC(II) = CC(III)-O_2-CC(II), E°_{cc} \qquad (1)$$

where the Roman numeral in parentheses indicates the oxidation state and $E°_{cc}$ is the standard oxidation potential of the carrier compound. Similarly, the standard half-cell reaction for oxidation of the electrocatalyst (EC) can be written as follows:

$$EC = EC^+ + e^-, E°_{ec} \qquad (2)$$

where $E°_{ec}$ is the oxidation potential of the electrocatalyst. Thus, $E°_{ec}$ will be less than $E°_{cc}$, providing a decreased potential for driving the oxidation of the carrier compound and release of oxygen.

The electrical potential of the electrocatalyst must not be too far below that of the oxygenated carrier compounds, or an unfavorable thermodynamic equilibrium will result. Usually, the electrocatalyst will have a potential below that of the carrier compound by about 0.1 to 0.5 volts, usually by about 0.2 to 0.3 volts.

Surprisingly, it has now been found that suitable electrocatalysts cannot be predicted based on their oxidation/reduction potentials relative to the carrier compounds. Such oxidation/reduction potentials can be made by measuring the potentials for both the electrocatalyst and the carrier compound by conventional techniques, typically using a calomel or other standard electrode. However, while a desirable oxidation/reduction potential would suggest that the electrocatalyst would be effective in promoting the release of oxygen, in fact many such electrocatalysts do not work with the carrier compounds of the present invention. Apparently, such electrocatalysts react irreversibly with the carrier compound subsequent to release of oxygen by the carrier compound. The thus-bound carrier compounds are incapable of further binding oxygen. Such properties render these electrocatalysts unsuitable for commercial applications.

As a result of such properties, it is necessary to screen potential electrocatalyst candidates further for their reactive tendencies with particular carrier compounds. Unfortunately, it is not possible to identify suitable candidates from an electrochemical series table. Only experimentation will determine whether or not a particular candidate will perform the electron transfer step adequately without subsequent reaction with the carrier compound.

Thus, the purpose of the electrocatalysts of the present invention is to provide a catalytic or low-energy pathway for the oxygen release process. They must not interfere in any other way with the action of the carrier compounds. Additionally, suitable electrocatalysts for use in the present invention are chosen based on the stability of the two species involved in the electron transfer at the electrode, i.e. both EC and EC+ are stable under the conditions used; the electron transfer at the electrode must be rapid; and the potential at which electron transfer occurs must be suitable. The suitable potential depends on the mechanism of the carrier oxidation reaction. The catalysts must also be soluble in the solvent conditions used.

Conveniently, initial selection may be made by testing the effectiveness of a candidate electrocatalyst in lowering the potential required to release oxygen in a coulometric experiment, as follows. Oxygenated carrier compound is placed in a cell having a working electrode and an auxiliary electrode. The electrodes are separated by an ion-permeable membrane, and the oxygenated carrier compound is in contact only with the working electrode. A suitable electrolyte is placed in contact with the auxiliary electrode. The voltage required to release oxygen from the oxygenated carrier compound can then be determined by stepping the voltage until oxygen release is detected, typically using a conventional oxygen probe. The experiment may then be repeated with the addition of an electrocatalyst candidate, either in solution or immobilized on the electrode, in order to determine the reduction in potential required for the release of oxygen. If the reduction is in the suitable range from about 0.1 to 0.5 volts, usually from about 0.2 to 0.4 volts, the electrocatalyst may be effective in reducing the energy consumption in an electrochemical cell as described above. However, after initial selection, the electrocatalyst must be further tested in EOC experiments, as described above, to determine whether it is compatible with the carrier compound and therefore suitable in the present invention.

Classes of electrocatalysts which are suitable for use in the present invention include anions, such as iodide, bromide, and nitrate; and organometallic compounds, such as ferrocene and ferrocene derivatives, cobaltocenes, nickelocenes, and metal carbonyls. Preferred electrocatalysts include ferrocene and substituted ferrocene derivatives, and iodide ions.

Figure 3:
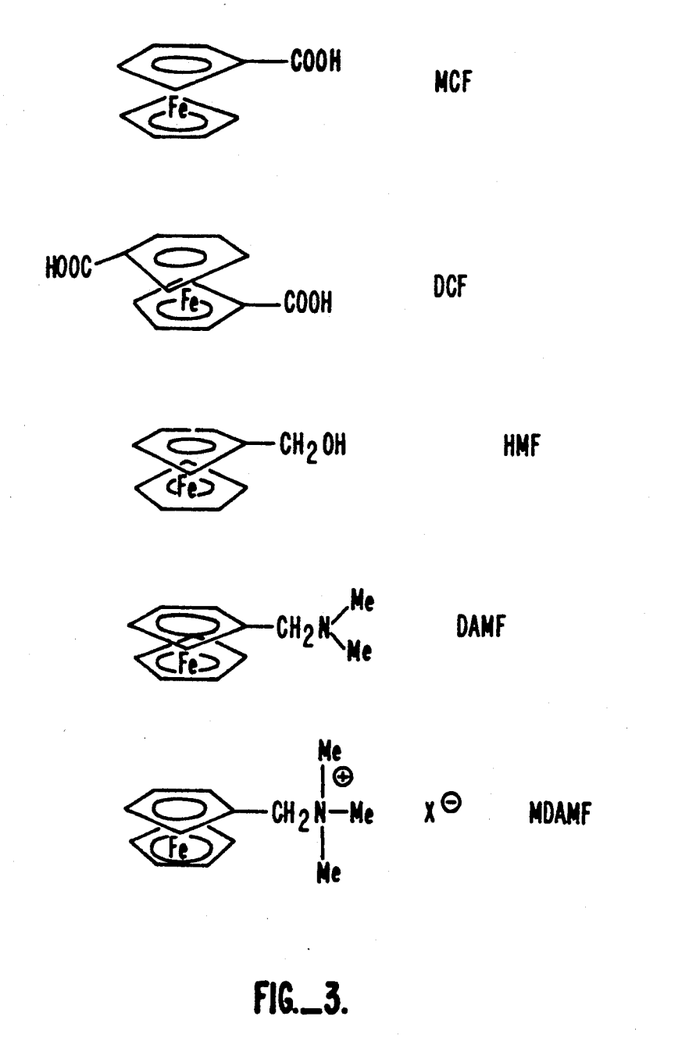
FIG. 3 shows the structures of certain ferrocene derivatives. "X" is a halogen atom.

Ferrocene and ferrocene derivatives are particularly suitable for use in the present invention. Ferrocene itself is insoluble in water so that when water is the solvent used in the EOC system, solubilizing groups must be incorporated into the ferrocene molecule. Such groups can be, for example, carboxylic acid, substituted amino groups, lower alkyl groups and substituted lower alkyl groups, and salts thereof, such as ammonium salts for example. Particular ferrocene derivatives which are useful in the present invention are ferrocene monocarboxylic acid (MCF), 1,1'-ferrocenedicarboxylic acid (DCF), hydroxymethylferrocene (HMF), dimethylaminomethylferrocene (DAMF), and the methylated quaternary ammonium halide salt of DAMF (MDAMF). The structures of these compounds are shown in FIG. 3. DAMF and MDAMF are preferred.

Once the electrocatalyst has been selected, it must be introduced to the oxygen extraction system. Usually, the electrocatalyst will be dissolved or mixed with the circulating carrier fluid, although it will sometimes be desirable to immobilize the electrocatalyst on the electrodes or on a support other than the electrodes. By including the electrocatalyst in the carrier fluid, the oxidation/reduction reactions may take place in the carrier fluid away from the electrode surfaces. This geometric effect increases the frequency of encounters between the carrier compounds and the electrocatalysts, and thus promotes the net electron transfer between the electrodes and the carrier compound. Such promotion is in addition to the primary catalytic effect, i.e., lowering of the energy required to transfer electrons between the electrodes and carrier compound, discussed above.

Depending on its solubility, the electrocatalyst may be present in the carrier fluid at a concentration from about 0.01 mM to about 1M, more usually from about 0.1 mM to about 100 mM. Usually, it will be desirable to maintain an electrocatalyst concentration having an equivalent ratio to the carrier compound concentration of at least 1:1000 (e.g., electrocatalyst:eq. carrier compound), usually at least 1:500, more usually at least 1:200, and frequently higher, with the upper limit being the solubility or the concentration where the electrocatalyst interferes with the ability of the carrier compound to take up oxygen. For the preferred electrocatalysts, a concentration of approximately 1 mM to 10 mM has been found effective.

The electrocatalyst may also be bound to a substrate, particularly when the electrocatalyst otherwise interferes with the oxygen uptake of the carrier compound. By immobilizing the electrocatalyst, and keeping it away from the loading station where oxygen is bound, such interference can be avoided. The method for binding the electrocatalyst to the solid phase will depend on both the nature of the electrocatalyst and the nature of the solid phase. Numerous binding and conjugation techniques for a wide variety of substances are described in the scientific and patent literatures, and immobilization methods for most combinations of electrocatalyst and solid phase material will be readily available.

The solid phase will usually, but not necessarily, be the electrode itself. It is also possible to bind the electrocatalyst to a solid phase which is maintained outside of the electrochemical cell. The electrocatalyst on such a remote solid phase is charged using a separate fluid circuit which carries additional liquid phase (mobile) electrocatalyst, which may be the same or a different electrocatalyst than that which is bound to the solid phase. By exposing the liquid phase to the electrochemical cell, the mobile electrocatalyst may be oxidized or reduced, as desired. The remote solid phase catalyst is oxidized or reduced by the mobile electrocatalyst. After clearing all mobile electrocatalyst, the remote solid phase is exposed to the carrier fluid which includes the oxygenated carrier compounds so that the solid phase may oxidize or reduce the carrier compounds to release oxygen therefrom. In this way, the electrocatalyst is kept from the loading station to avoid interference.

The electrodes of the electrochemical cell will be of conventional construction. The electrode material will be electrically conductive but chemically inert with the carrier fluid and carrier compounds under the operating conditions of the electrochemical cell, and is usually a metal or a carbon/graphite. Suitable metal electrodes include transition metals such as titanium, iron, nickel, copper, silver, platinum, gold, palladium, tin, tantalum, cobalt, ruthenium oxide, and alloys and mixtures thereof. Suitable carbon/graphite electrodes include glassy (amorphous) carbons, reticulated vitreous carbons, pyrolytic carbons, carbon felts, and the like.

The construction of the electrode will depend on the material type, with metal electrodes generally being in the form of plates, bars, and screens, or being sintered to form a highly porous structure. Metal electrodes may also be formed by depositing a film or layer of the metal on a nonconductive substrate, such as glass. The structure of carbon/graphite electrodes will depend upon the type of carbon. Glassy carbon electrodes are generally flat, polished surfaces while reticulated vitreous carbons are glass-like porous structures, typically pyrolyzed polyacrylonitriles. Pyrolytic carbons are produced by vapor phase deposition of carbon on a substrate, resulting in a polycrystalline structure with a high degree of atomic orientation.

Preferred is the use of carbon felt electrodes which are generally woven from yarns which are bundles of individual carbon monofilaments generally having a diameter in the range from about 1 to 50 $\mu$m, usually in the range from about 5 to 10 $\mu$m. The yarns will typically include from about 100 to 20,000 monofilaments, usually having from about 3,000 to 6,000 filaments. The denier of the yarns used as in fabricating the carbon felts will typically be in the range from about 500 to 5,000 mg/m, usually being in the range from about 1,000 to 2,000 mg/m. Denier is equal to the number of grams which yield 9,000 meters of the yarn or filament.

The yarns are woven by conventional weaving machines yielding large fabrics which may be cut into the desired dimensions for the electrode. Each electrode may employ a plurality of layers of the fabric, so that the final dimensions of the electrode may vary widely. Generally, the electrodes will have a height in the range from about 1 cm to 100 cm, a width in the range from about 1 cm to 100 cm, and a thickness in the range from about 0.1 cm to 10 cm. The particular dimensions chosen will depend primarily on the capacity of the electrochemical cell.

Carbon felts suitable for use in the present invention may be obtained commercially from suppliers such as FMI Fiber Materials, Inc., Biddleford, Me.; Hercules, Inc., Wilmington, Del.; Celanese Engineering, Chatham, N.J.; Ultra Carbon Corp., Bay City, Mich.; and Union Carbide Corp., Specialty Polymers and Composites Division, Danbury, Conn.

The present invention will employ a carrier fluid having carrier compounds capable of reversibly binding oxygen and carrying the bound oxygen from the loading station to the electrochemical cell. The carrier compounds should be soluble in the carrier fluid, and a variety of suitable natural and synthetic carrier compounds have been developed. Carrier compounds comprising a metal ion chelated to nitrogens of a cyclic tetradentate molecule or a porphin ring, are described in detail in U.S. Pat. Nos. 4,609,383 and 4,629,544, the disclosures of which have previously been incorporated herein by reference. The latter class of compounds are typified by naturally occurring oxygen carriers, such as hemoglobin, myoglobin, peroxidase, catalase, and various cytochromes.

Recently, a number of synthetic oxygen carrier compounds have been developed. The compounds include metal ions, usually cobalt, chelated to particular ligands. One example of such carrier compounds are those comprising linear, pentadentate polyalkylamine ligands and transition metal ions having the general formula:

wherein,
each of $R_1$ and $R_2$ is independently an organic group including a nitrogen coordinated to M;
each of m, n, o, and p is independently 1, 2, 3, or 4;
t is 0 or 1;
X is selected from the group consisting of 2,6-pyridyl, 2,6-piperidyl, 2,5-pyrrolyl, 2,5-imidazolyl, substituted heterocyclic amines, —O—, —S—, >P—$R_3$, and >N—$R_3$, where $R_3$ is hydrogen, lower alkyl, or aralkyl; and
M is a transition metal ion selected from titanium, manganese, chromium, iron, cobalt, nickel, copper, ruthenium, rhodium, palladium, osmium, iridium, and platinum.

Particular linear, pentadentate polyalkylamine ligands include 1,4,7,10,13-pentaazatridecane; 1,9-bis(2-pyridyl)-2,5,8-triazanonane; 1,10-bis(2-pyridyl)-2,5,9-triazadecane; 1,11-bis(2-pyridyl)-2,6,10-triazaundecane; 1,12-bis(2-pyridyl)-2,6,11-triazadodecane; 1,11-bis(2-pyridyl)-6-methyl-2,6,10-triazaundecane; 1,9-bis(2-(6-methylpyridyl))-2,5,8-triazanonane; 1,11-bis(2-(6-methylpyridyl))-2,6,10-triazaundecane; 2,6-bis(3-(1-(2-pyridyl)-2-azapropyl)pyridine; 2,6-bis(1-(4-(2-pyridyl)-2-azabutyl)pyridine; 2,6-bis(5-(1,4-diazapentyl))pyridine; and 2,6-bis(6-(1,5-diazahexyl))pyridine.

The preparation and use of the above pentadentate carrier compounds are described in detail in copending application Ser. No. 306,730, filed Feb. 3, 1989, the disclosure of which is incorporated herein by reference.

The carrier fluid is normally aqueous, but may be non-aqueous, particularly when the feedstock is exposed to the carrier-fluid without a separation membrane, e.g., by bubbling or sparging. Suitable non-aqueous carrier fluids include a variety of solvents, particularly aprotic solvents such as N,N'-dimethylformamide, benzene, dimethyl sulfoxide, nitriles, including acetonitrile and benzonitrile, propylene carbonate, acetone, various ethers, pyridine, and the like. Alcohols will also find use.

The majority of these carrier compounds bind in pairs to single oxygen molecules, usually with the carrier compound in a reduced oxidation state. For the ligand-metal ion complexes just described, the binding can be indicated as follows:

$$CC(II)—O_2—CC(II) \qquad (3)$$

where CC(II) is the carrier compound with the metal ion in a +2 oxidation state. The release of oxygen is then effected by oxidation of the carrier compound to the +3 oxidation state, with the electrocatalyst acting as an intermediate. Although the exact mechanism will vary with particular carrier compounds and electrocatalysts, the overall oxidation will proceed as follows:

$$2EC = 2EC^+ + 2e^- \qquad (4)$$

$$2EC^+ + CC(II)—O_2—CC(II) = O_2 + 2EC + 2CC(III) \qquad (5)$$

The oxygen extraction systems of the present invention are operated by continuously circulating the carrier fluid between the electrochemical cell and the oxygen loading station. Particular methods for operating the apparatus are described in detail in U.S. Pat. Nos. 4,609,383 and 4,629,544, which have been previously incorporated herein by reference. The variables of operation include concentration of the carrier compound in the carrier fluid, flow rate of the carrier fluid through the apparatus, voltage applied across the electrodes, current load consumed by the electrodes, electrode area, and the volume of oxygen produced by the apparatus. When employing the ligand-metal ion carrier compounds described above, it has been found that oxidation of the carrier compounds and release of oxygen is promoted by controlling pH, usually in the range from 3 to 12, more usually in the range from 6 to 8. Typical values for these parameters are set forth in Table 1 below.

TABLE 1

|  | Broad Range | Narrow Range |
| --- | --- | --- |
| Carrier Compound Concentration | 1 mM–1 M | 10 mM–500 mM |
| Flow Rate of Carrier Fluid | 0–10$^5$ L/min | 50 ml/min–100 L/min |
| Voltage* | 0.1–2.0 | 0.2–1.0 |
| Current Density | 100 μA–5 A/cm$^2$ | 1 mA–100 mA/cm$^2$ |
| Electrode Area | 1 cm$^2$–10$^5$ m$^2$ | 1 cm$^2$–100 m$^2$ |
| Volume O$_2$ Produced | 0.1 mL–1000 m$^3$/min | 1 mL–1000 L/min |

TABLE 1-continued

| | Broad Range | Narrow Range |
|---|---|---|
| pH | 3–12 | 6–8 |

*These voltage ranges apply to a cell consisting of a single anode and cathode pair. For bipolar stacks, the voltage will be proportionally higher.

As demonstrated more fully in the Experimental section hereinafter, using the electrocatalysts of the present invention substantially reduces the operating voltage required to effect the oxidation/reduction of the carrier compounds with the accompanying release of oxygen. Typically, operating voltages will be decreased by about 0.1 to 0.5 volts, usually about 0.2 to 0.4 volts, when the electrocatalysts of the present invention are employed. This decrease, in turn, provides for a substantial reduction in energy consumption as the current load remains constant for a given volume of oxygen.

The following examples are offered by way of illustration and not by way of limitation.

EXPERIMENTAL

The effect of the electrocatalysts of the present invention in enhancing oxygen extraction was tested by cyclic voltammetry and coulometry, and in the electrochemical oxygen cell (EOC) systems described in U.S. Pat. Nos. 4,602,987 and 4,609,383.

EXAMPLE 1

Figure 2:
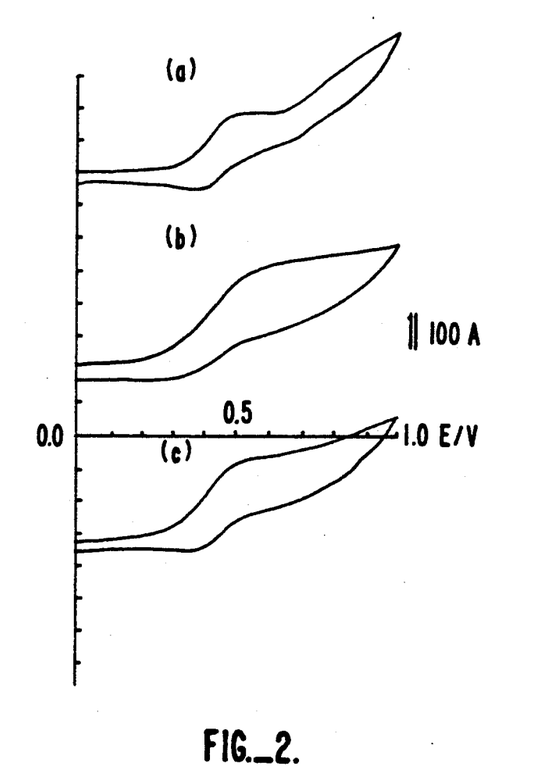
FIG. 2 is a cyclic voltammagram demonstrating the effect of pH on the ability of 1,1'-ferrocenedicarboxylic acid (5 mM) to mediate electron transfer to air-saturated cobalt 1,9-bis-(2-pyridyl)-2,5,8-triazanonane.

In cyclic voltammetry, a small electrochemical cell was used which consisted of a flask containing the carrier fluid in which three electrodes were immersed. These were the counter electrode (platinum), the reference electrode (usually a saturated calomel electrode), and a small working electrode (graphite, glassy carbon, platinum, gold or other suitably inert metal). A potential difference was applied between the working and reference electrodes, and this difference was varied in a linear fashion until reaching a switching value where the direction of the potential variation was reversed. The current flowing at the working electrode was monitored as a function of potential, with the resulting plot being the cyclic voltammogram. FIG. 2 shows such plots for a solution of 1,1'-ferrocenedicarboxylic acid in a buffered, saline solution at different acidities in the presence of a large excess of oxygen carrier (cobalt 1,9-bis(2-pyridyl)-2,5,8-triazanonane). It can be clearly seen that the shape of the plot is dependent upon the pH of the solution. FIG. 2(a), recorded at pH 7.3, resembles most closely the behavior of the 1,1'-ferrocenedicarboxylic acid in the absence of the oxygen carrier, and this indicates that there is very little interaction between the two species under these conditions. FIG. 2(b), in contrast, shows a marked increase in the oxidation current at pH 10.1 with 0.4–0.5 V and complete removal of the reduction current at 0.4 V on the reverse sweep. At this pH, then, there is a large interaction between the species. FIG. 2(c), which was recorded using a pH intermediate between those used in FIGS. 2(a) and 2(b), shows intermediate behavior. In the absence of the 1,1'-ferrocenedicarboxylic acid there is little or no current flowing at 0.4 V, so that there is no oxidation of the oxygen carrier at this potential normally. The increase in the current of the 1,1'-ferrocenedicarboxylic acid shown in FIGS. 2(b) and 2(c) indicates that oxidation of the carrier is occurring through the mediation of electron transfer by the ferrocene species. The dependence of this mediation on the pH of the solution indicates that the reactivity of the carrier controls this process since the voltammograms of 1,1'-ferrocenedicarboxylic acid alone in solution show no pH dependence. The voltammograms of the oxygen carrier complexes are very dependent upon the pH.

EXAMPLE 2

This coulometric experiment involved the use of a larger electrode than in cyclic voltammetry (Example 1) and the measurement of the oxygen produced, as well as the current as a function of the applied potential. A cell was used which comprised two compartments separated by an ion exchange membrane or microporous separator. One compartment was the counter-electrode compartment and contained potassium ferricyanide in the buffered aqueous solution of interest and the counter-electrode itself, which was reticulated vitreous carbon (2 cm × 1 cm). The working electrode compartment contained the oxygen carrier solution, a reference electrode (silver/silver chloride), the working electrode (carbon felt, 2 cm × 1 cm), and a Clark oxygen electrode probe (Yellow Springs Instruments, Model 5775). The experiment consisted of saturating the carrier solution with air by bubbling and then applying a potential difference between the working and reference electrodes by means of a potentiostat (BAS CV-27). The potential was increased in steps of 100–200 mV from 0 to 0.7 volts, and the charge passed and the oxygen released was monitored. The potential was then set to a value sufficiently negative to reduce all or most of the oxidized carrier back to its original form. This value was usually in the range of 0 to −0.2 V. The working electrode compartment was then resaturated with air and the procedure repeated to ensure that the carrier can complete the cycle. Sometimes the oxidized carrier was not reduced fully back to its original form before the solution was resaturated with air. This was to allow the behavior of the carrier to be studied while it was a mixture of its oxidized and reduced forms. The above cyclization procedure was repeated several times on the same solution to confirm the repeatability of the system.

Once the behavior of the carrier was ascertained, the electrocatalyst was added to the working electrode compartment and the potential step procedure was repeated. Table 2 shows the results of a number of such experiments using three different oxygen carrier compounds and several different electrocatalysts. It is clear from the response of the oxygen probe electrode that oxygen is released at a lower potential in the presence of the electrocatalysts than in their absence, and the charge passed demonstrates that the electron transfer proceeds through the mediation of the electrocatalyst at these lower potentials. To check the efficacy of the electrocatalyst, the cycle was repeated several times with the same solution containing the catalyst. It was found that the substituted ferrocenes and potassium iodide worked over all cycles.

Comparable tests following the above procedures were run using 3-methoxycatechol. An increased amount of oxygen over the control was produced for one cycle, but the amount greatly decreased thereafter. It was determined that 3-methoxycatechol irreversibly bound to the carrier compound. Potassium ferricyanide and 2,3-dicyanohydroquinone were tested in the same manner for electrocatalytic activity and were found to produce decreased amounts of oxygen compared to the controls.

TABLE 2

Coulometry of Oxygen Carriers in the Presence and Absence of Electrocatalysts

| Carrier Compound | Electrocatalyst | pH | E/Volts | Q/coulombs* | $O_2$/mV |
|---|---|---|---|---|---|
| Cobalt - 1,9-bis-(2-pyridyl)-2,5,8-triazanonane 2Cl (4 mM) | | 9.4 | 0.2 | 0.02 | 0 |
| | | | 0.4 | 0.09 | 10 |
| | | | 0.5 | 0.29 | 30 |
| | | | 0.6 | 0.58 | 52 |
| | | | 0.7 | 1.62 | 113 |
| Cobalt - 1,9-bis(2-pyridyl)-2,5,8-triazanonane 2Cl (4 mM) | 1,1'-Ferrocene-dicarboxylic acid (1 mM) | 9.4 | 0.2 | 0 | 0 |
| | | | 0.35 | 0.93 | 78 |
| | | | 0.4 | 1.54 | 99 |
| Cobalt - 1,9-bis-(2-pyridyl)-2,5,8-triazanonane 2Cl (4 mM) | | 6.9 | 0.3 | 0.05 | 0 |
| | | | 0.5 | 0.5 | 45 |
| | | | 0.6 | 1.2 | 83 |
| | | | 0.7 | 2.63 | 184 |
| Cobalt - 1,9-bis-(2-pyridyl)-2,5,8-triazanonane 2Cl (4 mM) | KI (1 mM) | 6.9 | 0.4 | 2.17* | 0 |
| | | | 0.45 | 2.73 | 112 |
| | | | 0.6 | 5.0 | 298 |
| Cobalt - 1,9-bis-(2-pyridyl)-2,5,8-triazanonane 2Cl (4 mM) | | 7.3 | 0.3 | 0.03 | 0 |
| | | | 0.5 | 0.21 | 18 |
| | | | 0.6 | 0.7 | 65 |
| | | | 0.7 | 2.37 | 167 |
| Cobalt - 1,9-bis-(2-pyridyl)-2,5,8-triazanonane 2Cl (4 mM) | Ferrocene-carboxylic acid | 7.3 | 0.2 | 1.56* | 9 |
| | | | 0.25 | 2.01 | 67 |
| | | | 0.3 | 2.31 | 85 |
| | | | 0.35 | 2.4 | 85 |
| Cobalt - 1,11-bis-(2-pyridyl)-2,6,10-triazaundecane 2Cl (4 mM) | | 7.5 | 0.1 | 0.09 | 16 |
| | | | 0.2 | 0.34 | 69 |
| | | | 0.3 | 0.45 | 76 |
| | | | 0.4 | 0.58 | 86 |
| | | | 0.5 | 0.9 | 115 |
| | | | 0.6 | 1.47 | 174 |
| | | | 0.7 | 2.07 | 174 |
| Cobalt - 1,11-bis-(2-pyridyl)-2,6,10-triazaundecane 2Cl (4 mM) | 1,1'-Ferrocene-dicarboxylic acid | 7.5 | 0.1 | 0.05 | 11 |
| | | | 0.2 | 0.18 | 28 |
| | | | 0.3 | 0.76 | 114 |
| | | | 0.4 | 2.02 | 218 |
| Cobalt - 1,10-bis-(2-pyridyl)-2,5,9-triazadecane 2Cl (4 mM) | | 7.4 | 0.3 | 0.16 | 15 |
| | | | 0.4 | 0.64 | 26 |
| | | | 0.5 | 2.59 | 68 |
| | | | 0.6 | 4.23 | 105 |
| | | | 0.7 | 5.83 | 117 |
| Cobalt - 1,10-bis-(2-pyridyl)-2,5,9-triazadecane 2Cl (4 mM) | 1,1'-Ferrocene-dicarboxylic acid | 7.4 | 0.1 | 0.08 | 16 |
| | | | 0.2 | 0.21 | 34 |
| | | | 0.3 | 0.48 | 56 |
| | | | 0.4 | 1.00 | 71 |
| Cobalt - 1,10-bis-(2-pyridyl)-2,5,9-triazadecane 2Cl (4 mM) | 3-methoxycate-chol (1 mM) | 7.6 | 0.35 | 0.24 | 40 |
| | | | 0.45 | 0.42 | 92 |
| | | | 0.6 | 0.7 | 112 |
| | | | 0.65 | 1.05 | 182 |
| Cobalt - 1,11-bis-(2-pyridyl)-2,6,10-triazaundecane 2Cl (4 mM) | 3-methoxycate-chol (1 mM) | 7.5 | 0.15 | 0.25 | 10 |
| | | | 0.25 | 0.89 | 25 |
| | | | 0.4 | 1.14 | 55 |
| | | | 0.6 | 1.51 | 155 |
| Cobalt - 1,11-bis-(2-pyridyl)-2,6,10-triazaundecane 2Cl (4 mM) | | 7.1 | 0.35 | 0.18 | 31 |
| | | | 0.55 | 0.62 | 86 |
| | | | 0.65 | 1.07 | 126 |
| Cobalt - 1,11-bis-(2-pyridyl)-2,6,10-triazaundecane 2Cl (4 mM) | hydroxymethyl-ferrocene | 7.1 | 0.25 | 0.39 | 62 |
| | | | 0.35 | 0.45 | 71 |
| | | | 0.5 | 0.6 | 76 |

Conditions: 0.5 M KCl, 0.1 M K2HPO4 adjusted with KOH, auxiliary compartment contains ca. 5 mM K3Fe(CN)4.
*Where the number of coulombs is greater than 0 at the start of the experiment, the carrier was not reduced back to the Co(II) form before the solution was resaturated with air. Thus, Q-1.53 means that 1.53 mM of the Co is in the Co(III) form.

EXAMPLE 3

Using the electrochemical oxygen cell system described in U.S. Pat. Nos. 4,602,987 and 4,609,383, the operation of the electrocatalysts of the present invention was demonstrated in a flowing, cycling system where large electrodes (25 cm²) were used and significant volumes of oxygen were produced (0.2 to 2 mL/min). In this experiment, the overall cell voltage was controlled since the product of the voltage and the current gives the power required to extract the oxygen. A solution of cobalt chloride (100 mM) and 1,9-bis(2-pyridyl)-2,5,8-triazanonane (100 mM) in 0.8M sodium chloride/water was oxidized in the electrochemical cell so that half of the cobalt complex was in the reduced form (Co(II)) and half was in the oxidized form (Co(III)). This solution was circulated in the electrochemical oxygen cell system and voltage was applied. It was found that 0.3 mL/min of oxygen was produced at 0.94 V. The current required was 94 mA, which corresponds to a value of 297 W/L-min of oxygen produced. When ferrocenecarboxylic acid (MCF; 1 mM concentration) was added to this solution, 0.3 mL/min of oxygen was produced at 0.7 V using 86 mA of current. This corresponds to a power requirement of 202 W/L-min of oxygen produced.

A second solution was prepared in the same manner, and again 0.3 mL/min of oxygen was obtained at 0.94 V using 109 mA of current and requiring 324 W/L-min of oxygen. When potassium iodide was added to this solution (1 mM concentration), 0.3 mL/min of oxygen was obtained at 0.75 V using 82 mA, corresponding to a power requirement of 200 W/L-min of oxygen.

A third solution prepared in the same manner gave 0.3 mL/min of oxygen at 0.86 V using 123 mA and 343 W/L-min of oxygen. After addition of 1,1'-ferrocenedicarboxylic acid (DCF; 1 mM concentration), 0.3 mL/min of oxygen was obtained at 0.69 V using 88 mA current and requiring 200 W/L-min of oxygen.

However, while there was an increase of current and oxygen output at low voltages with the MCF and the DCF, at higher voltages (of about 1.0 V and above) the oxygen output with each of these catalysts decreased in comparison to the controls.

Figure 4A:
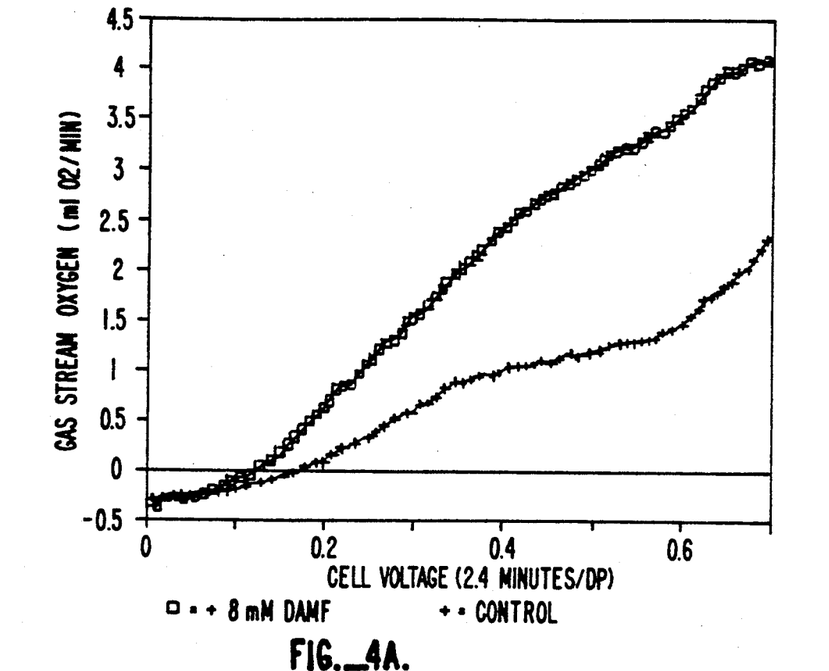
FIGS. 4(a) and (b) shows the results of an electrochemical oxygen cell (EOC) experiment utilizing cobalt 1,11-bis-(2-pyridyl)-2,6,10-triazaundecane as the carrier and dimethylaminomethylferrocene as the electrocatalyst.
Figure 4B:
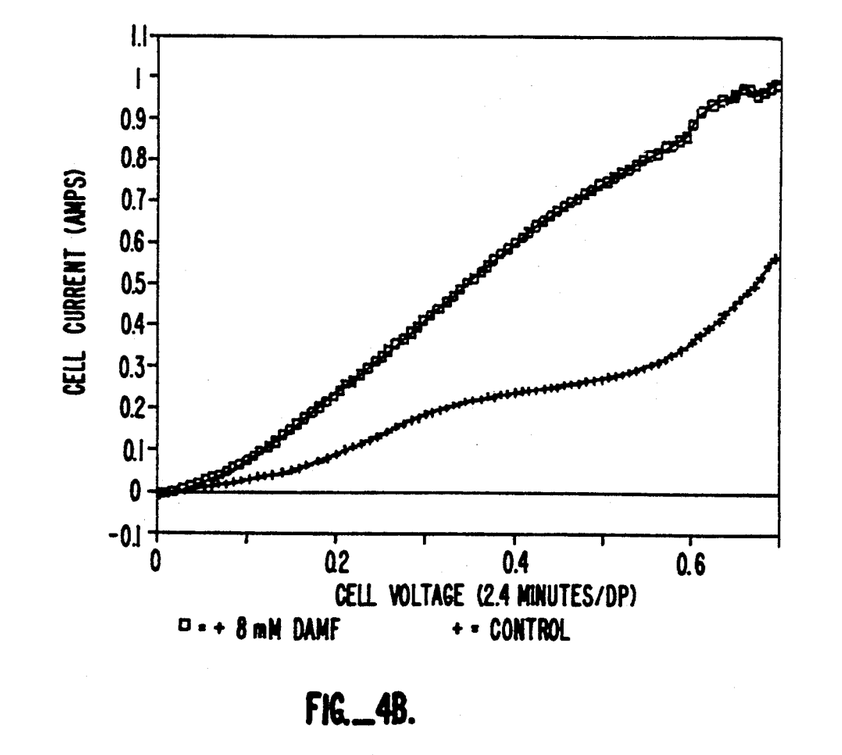

In the same manner as above, a solution of cobalt chloride (400 mM) and 1,11-bis(2-pyridyl)-2,6,10-triazaundecane (400 mM) in 1.5M potassium chloride/water was prepared and circulated in the EOC system. The results, with and without addition of 8 mM of dimethylaminomethylferrocene (DAMF), are presented in FIG. 4. Further experiments showed that oxygen output at higher voltages remained larger with the DAMF than with the control.

Figure 5A:
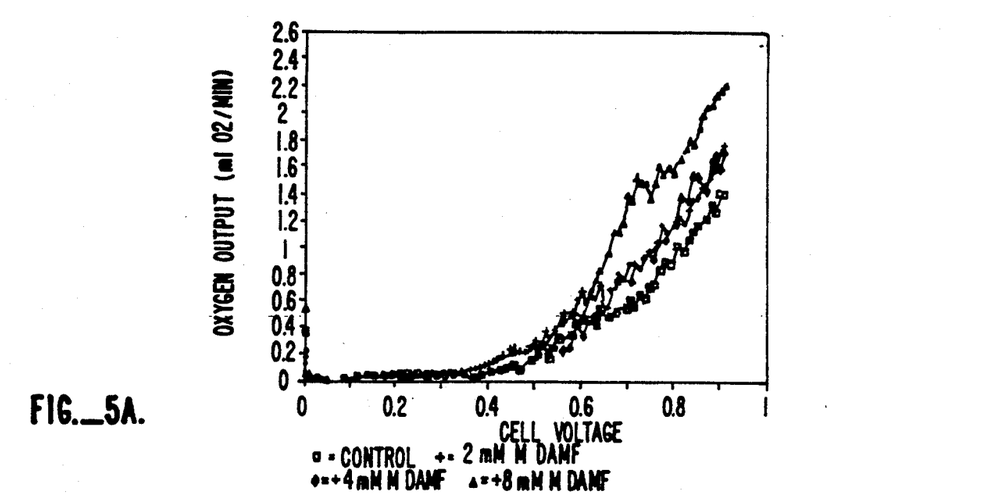
FIGS. 5(a)–(c) shows the results of an EOC experiment utilizing cobalt 1,10-bis-(2-pyridyl)-2,5,9-triazadecane as the carrier and the methylated ammonium bromide salt of dimethylaminomethylferrocene as the electrocatalyst.
Figure 5B:
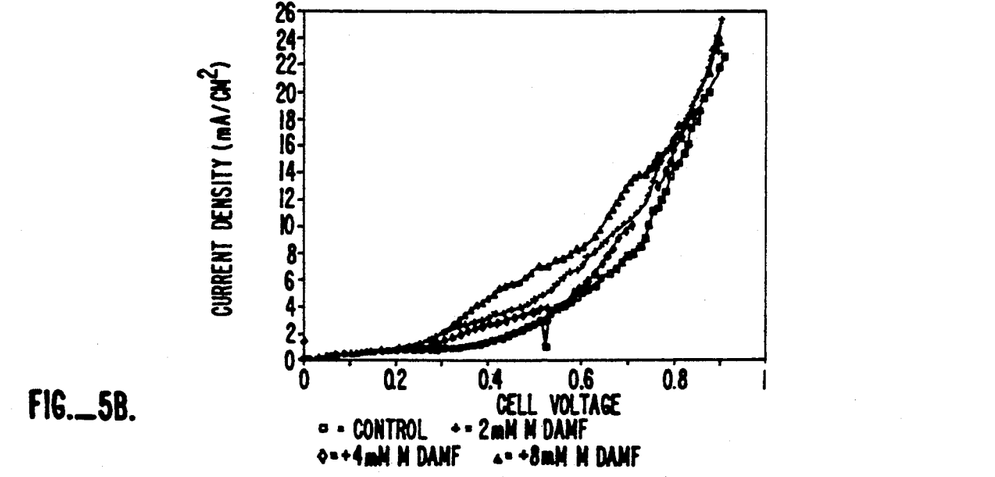
Figure 5C:
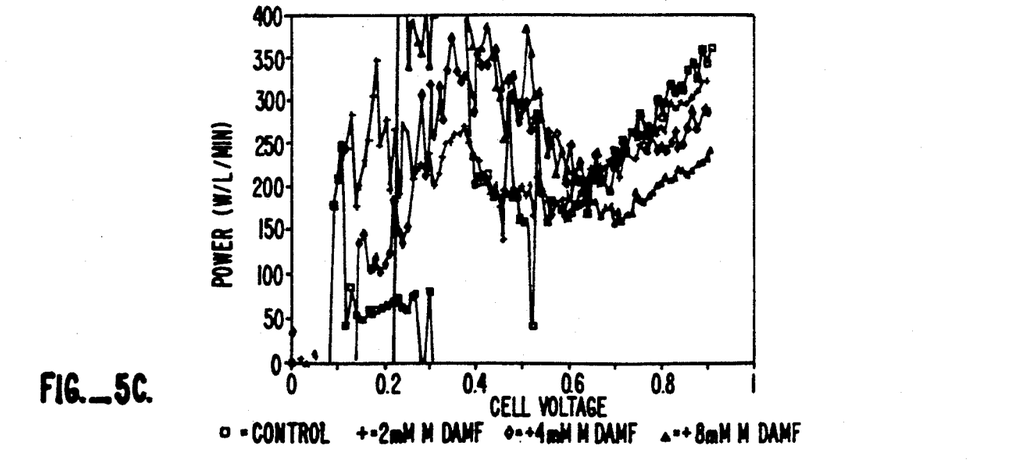

Also in the same manner, a solution of cobalt chloride (400 mM) and 1,10-bis(2-pyridyl)-2,5,9-triazadecane (400 mM) in 3.5M sodium chloride/water was prepared and circulated in the EOC system. The results, with and without addition of the methylated quaternary ammonium bromide salt of dimethylaminomethylferrocene (MDAMF, where X is bromo) at 2 mM, at 4 mM and at 8 mM, are presented in FIG. 5. Further experiments showed that oxygen output at higher voltages remained larger with the MDAMF than with the control.

Although the foregoing invention has been described in some detail by way of illustration and example for purposes of clarity of understanding, it will be obvious that certain changes and modifications may be practiced within the scope of the appended claims.

What is claimed is:

1. A method for extracting molecular oxygen from a fluid mixture feedstock, said method comprising:
   exposing a carrier fluid to the feedstock, said carrier fluid including a carrier compound able in a first oxidation state of binding oxygen and in a second oxidation state of releasing bound oxygen;
   exposing the carrier fluid to a first electrode of an electrochemical cell using an electrocatalyst to transfer electrons between the electrode and the carrier compound, whereby the first oxidation state of the carrier compound is converted to the second oxidation state to release bound oxygen, and wherein the electrocatalyst is selected from the group consisting of substituted ferrocenes and iodide ion; and
   exposing the carrier fluid to a second electrode of the electrochemical cell, whereby the carrier compound is converted back to the first oxidation state so that said carrier compound is again able to bind oxygen; and
   wherein the carrier compound is of the formula:

where,
   each of $R_1$ and $R_2$ is independently an organic group including a nitrogen coordinated to M;
   each of m, n, o, and p is independently 1, 2, 3, or 4;
   t is 0 or 1;
   X is selected from the group consisting of substituted heterocyclic amines, —O—, —S—, >P—$R_3$, and >N—$R_3$, where $R_3$ is hydrogen, lower alkyl, or aralkyl; and
   M is a transition metal ion selected from titanium, manganese, chromium, iron, cobalt, nickel, copper, ruthenium, rhodium, palladium, osmium, iridium, and platinum.

2. A method as in claim 1, wherein the carrier compound in the carrier fluid is a metal ion chelated to a ligand selected from the group consisting of 1,4,7,10,13-pentaazatridecane; 1,9-bis(2-pyridyl)-2,5,8-triazanonane; 1,10-bis(2-pyridyl)-2,5,9-triazadecane; 1,11-bis(2-pyridyl)-2,6,10-triazaundecane; 1,12-bis(2-pyridyl)-2,6,11-triazadodecane; 1,11-bis(2-pyridyl)-6-methyl-2,6,10-triazaundecane; 1,9-bis(2-(6-methylpyridyl))-2,5,8-triazanonane; 1,11-bis(2-(6-methylpyridyl))-2,6,10-triazaundecane; 2,6-bis(3-(2-pyridyl)-2-azapropyl)pyridine; 2,6-bis(1-(4-(2-pyridyl)-2-azabutyl)pyridine; 2,6-bis(5-(1,4-diazapentyl))pyridine; and 2,6-bis(6-(1,5-diazahexyl))pyridine.

3. A method as in claim 1, wherein the electrocatalyst is mobile in the carrier fluid.

4. A method as in claim 1, wherein the electrocatalyst is immobilized on at least one of the electrodes.

5. A method as in claim 1, wherein the electrocatalyst is immobilized on a substrate other than an electrode, further comprising the step of circulating an electrocatalyst between the electrodes and the other substrate so that the immobilized electrocatalyst may be oxidized and reduced.

6. A method as in claim 1, wherein the electrocatalyst is selected from the group consisting of iodide ions and substituted ferrocene, where the ferrocene is substituted with carboxylic acid, substituted amino groups, lower alkyl groups and substituted lower alkyl groups, and salts thereof.

7. A method as in claim 6, wherein the electrocatalyst is selected from the group consisting of iodide ions, ferrocene monocarboxylic acid, 1,1'-ferrocenedicarboxylic acid, hydroxymethylferrocene, dimethylaminomethylferrocene, and the methylated quaternary ammonium bromide or chloride salt of dimethylaminomethylferrocene.

8. A method as in claim 1, wherein the carrier fluid is at a pH in the range from about 5 to 9.

9. A method as in claim 1, wherein the electrocatalyst is present at a concentration from about 0.01 mM to 1M.

10. A method as in claim 1, wherein a voltage is applied across the electrodes, said voltage being from about 0.1 to 0.5 volts less than the uncatalyzed cell potential of the oxygenated carrier compound under the conditions of the cell.

11. A method as in claim 1, wherein X is a substituted heterocyclic amine selected from the group consisting of 2,6-pyridyl, 2,6-piperidyl, 2,5-pyrrolyl, and 2,5-imidazolyl.

12. An improved method for extracting molecular oxygen from a fluid mixture feedstock of the type wherein a carrier fluid is circulated between a loading station and an electrochemical cell having a pair of electrodes, wherein said carrier fluid includes a carrier compound able in a first oxidation state of binding oxygen and in a second oxidation state of releasing bound oxygen, said carrier compound having the formula:

where,
each of $R_1$ and $R_2$ is independently an organic group including a nitrogen coordinated to M;
each of m, n, o, and p is independently 1, 2, 3, or 4;
t is 0 or 1;
X is selected from the group consisting of substituted heterocyclic amines, $-O-$, $-S-$, $>P-R_3$, and $>N-R_3$, where $R_3$ is hydrogen, lower alkyl, or aralkyl; and
M is a transition metal ion selected from titanium, manganese, chromium, iron, cobalt, nickel, copper, ruthenium, rhodium, palladium, osmium, iridium, and platinum;
whereby the carrier compound is converted to the first oxidation state by one electrode of the electrochemical cell in order to bind oxygen at the loading station and the carrier compound is converted to the second oxidation state by the other electrode in order to release oxygen, said improvement comprising:
providing an electrocatalyst selected from the group consisting of substituted ferrocenes and iodide ion, to promote electron transfer between said electrode and the carrier compound proximate at least one of the electrodes, whereby the energy required to oxidize or reduce the carrier compound is decreased.

13. An improved method as in claim 12, wherein the carrier compound in the carrier fluid is a metal ion chelated to a ligand selected from the group consisting of 1,4,7,10,13-pentaazatridecane; 1,9-bis(2-pyridyl)-2,5,8-triazanonane; 1,10-bis(2-pyridyl)-2,5,9-triazadecane; 1,11-bis(2-pyridyl)-2,6,10-triazaundecane; 1,12-bis(2-pyridyl)-6,11-triazadodecane; 1,11-bis(2-pyridyl)-6-methyl-2,6,10-triazaundecane; 1,9-bis(2-(6-methylpyridyl)-2,5,8-triazanonane; 1,11-bis(2-(6-methylpyridyl)-2,6,10-triazaundecane; 2,6-bis(3-(2-pyridyl)-2-azapropyl)pyridine; 2,6-bis(1-(4-(2-pyridyl)-2-azabutyl)-pyridine; 2,6-bis(5-(1,4-diazapentyl))pyridine; and 2,6-bis(6-(1,5-diazahexyl))pyridine.

14. An improved method as in claim 12, wherein the electrocatalyst is mobile in the carrier fluid.

15. An improved method as in claim 12, wherein the electrocatalyst is immobilized on at least one of the electrodes.

16. An improved method as in claim 12, wherein the electrocatalyst is immobilized on a substrate other than an electrode, further comprising the step of circulating an electrocatalyst between the electrodes and the other substrate so that the immobilized electrocatalyst may be oxidized and reduced.

17. An improved method as in claim 12, wherein the electrocatalyst is selected from the group consisting of iodide ions and substituted ferrocene, where the ferrocene is substituted with carboxylic acid, substituted amino groups, lower alkyl groups and substituted lower alkyl groups, and salts thereof.

18. An improved method as in claim 12, wherein the electrocatalyst is selected from the group consisting of iodide ions, ferrocene monocarboxylic acid, 1,1'-ferrocenedicarboxylic acid, hydroxymethylferrocene, dimethylaminomethylferrocene, and the methylated quaternary ammonium bromide or chloride salt of dimethylaminomethylferrocene.

19. An improved method as in claim 12, wherein the carrier fluid is at a pH in the range from about 5 to 9.

20. An improved method as in claim 12, wherein the electrocatalyst is present at a concentration from about 0.01 mM to 1M.

21. An improved method as in claim 12 wherein a voltage is applied across the electrodes, said voltage being from about 0.1 to 0.5 volts less than the uncatalyzed cell potential of the oxygenated carrier compound under the conditions of the cell.

22. A method as in claim 12, wherein X is a substituted heterocyclic amine selected from the group consisting of 2,6-pyridyl, 2,6-piperidyl, 2,5-pyrrolyl, and 2,5-imidazolyl.

23. An electrochemical system for extracting molecular oxygen from a fluid mixture feedstock, said system comprising:
an oxygen loading station;
an electrochemical cell including a pair of electrodes;
a voltage source connected to the electrodes;
a carrier fluid which circulates between the electrodes of the electrochemical cell and the oxygen loading station, said carrier fluid including a carrier compound able in a first oxidation state of binding molecular oxygen and in a second oxidation state of releasing bound oxygen, said carrier compound having the formula:

where,
each of $R_1$ and $R_2$ is independently an organic group including a nitrogen coordinated to M;
each of m, n, o, and p is independently 1, 2, 3, or 4;
t is 0 or 1;
X is selected from the group consisting of substituted heterocyclic amines, $-O-$, $-S-$, $>P-R_3$, and $>N-R_3$, where $R_3$ is hydrogen, lower alkyl, or aralkyl; and
M is a transition metal ion selected from titanium, manganese, chromium, iron, cobalt, nickel, copper, ruthenium, rhodium, palladium, osmium, iridium, and platinum; and
an electrocatalyst in proximity to at least one of the electrodes, said electrocatalyst selected from the group consisting of substituted ferrocenes and iodide ion.

24. An electrochemical system as in claim 23, wherein the oxygen loading station includes an oxygen-permeable membrane.

25. An electrochemical system as in claim 23, wherein the carrier compound in the carrier fluid is a metal ion chelated to a ligand selected from the group consisting of 1,4,7,10,13-pentaazatridecane; 1,9-bis(2-pyridyl)-2,5,8-triazanonane; 1,10-bis(2-pyridyl)-2,5,9-triazadecane; 1,11-bis(2-pyridyl)-2,6,10-triazaundecane; 1,12-bis(2-pyridyl)-2,6,11-triazadodecane; 1,11-bis(2-pyridyl)-6-methyl-2,6,10-triazaundecane; 1,9-bis(2-(6-methylpyridyl)-2,5,8-triazanonane; 1,11-bis(2-(6-methylpyridyl)-2,6,10-triazaundecane; 2,6-bis(3-(2-pyridyl)-2-azapropyl)pyridine; 2,6-bis(1-(4-(2-pyridyl)-2-azabutyl)pyridine; 2,6-bis(5-(1,4-diazapentyl))pyridine; and 2,6-bis(6-(1,5-diazahexyl))pyridine.

26. An electrochemical system as in claim 23, wherein the electrocatalyst is mobile in the carrier fluid.

27. An electrochemical system as in claim 23, wherein the electrocatalyst is immobilized on at least one of the electrodes.

28. An electrochemical system as in claim 23, wherein the electrocatalyst is bound to a support outside of the electrochemical cell, and non-bound electrocatalyst is circulated between the electrochemical cell and the immobilized electrocatalyst in order to effect oxidation and reduction of the immobilized electrocatalyst.

29. An electrochemical system as in claim 23, wherein the electrocatalyst is selected from the group consisting of iodide ions and substituted ferrocene, where the ferrocene is substituted with carboxylic acid, substituted amino groups, lower alkyl groups and substituted lower alkyl groups, and salts thereof.

30. An electrochemical system as in claim 29, wherein the electrocatalyst is selected from the group consisting of iodide ions, ferrocene monocarboxylic acid, 1,1'-ferrocenedicarboxylic acid, hydroxymethylferrocene, dimethylaminomethylferrocene, and the methylated quaternary ammonium bromide or chloride salt of dimethylaminomethylferrocene.

31. An electrochemical system as in claim 23, wherein X is a substituted heterocyclic amine selected from the group consisting of 2,6-pyridyl, 2,6-piperidyl, 2,5-pyrrolyl, and 2,5-imidazolyl.

* * * * *

UNITED STATES PATENT AND TRADEMARK OFFICE
CERTIFICATE OF CORRECTION

PATENT NO. : 5,017,274
DATED : May 21, 1991
INVENTOR(S) : John B. Kerr et al.

It is certified that error appears in the above—identified patent and that said Letters Patent is hereby corrected as shown below:

Column 1, line 5, please insert the following paragraph:

--This invention was made with Government support under contract N00014-87-C-0335 awarded by the Department of Navy. The Government has certain rights in the invention.--

Signed and Sealed this

Fourth Day of May, 1993

Attest:

MICHAEL K. KIRK

Attesting Officer

Acting Commissioner of Patents and Trademarks